(12) United States Patent
McDonald, II et al.

(10) Patent No.: US 7,946,707 B1
(45) Date of Patent: May 24, 2011

(54) EYE DOMINANCE EVALUATION APPARATUS AND METHOD

(76) Inventors: James Edward McDonald, II, Fayetteville, AR (US); Randolph Blake, Nashville, TN (US); Eunice Yang, Nashville, TN (US)

( * ) Notice: Subject to any disclaimer, the term of this patent is extended or adjusted under 35 U.S.C. 154(b) by 0 days.

(21) Appl. No.: 12/658,207

(22) Filed: Feb. 4, 2010

Related U.S. Application Data

(60) Provisional application No. 61/206,864, filed on Feb. 5, 2009.

(51) Int. Cl.
*A61B 3/02* (2006.01)
(52) U.S. Cl. .................. 351/239; 351/203; 351/243
(58) Field of Classification Search .................. 351/203, 351/222, 223, 237–243
See application file for complete search history.

(56) References Cited

U.S. PATENT DOCUMENTS

| | | | |
|---|---|---|---|
| H293 H | 6/1987 | Task et al. ................ | 351/243 |
| 4,971,434 A * | 11/1990 | Ball ........................ | 351/224 |

OTHER PUBLICATIONS

Collins, M.J., & Goode, A. (1994). Interocular blur suppression and monovision. *Acta Ophthalmologica*, 72(3), 376-380.
Handa, T., Mukuno, K., Uozato, H., Niida, T., Shoji, N., & Shimizu, K. (2004a). Effects of dominant and nondominant eyes in binocular rivalry. *Optometry and vision science*, 81(5), 377-382.
Handa, T., Mukuno, K., Uozato, H., Niida, T., Shoji, N., Minei, R., Nitta, M., & Shimizu, K. (2004b). Ocular dominance and patient satisfaction after monovision induced by intraocular lens implantation. *Journal of Cataract Refractive Surgery*, 30, 769-774.
Handa, T., Uozato, H., Higa, R., Nitta, M., Kawamorita, T., Ishikawa, H., Shoji, N., & Shimizu, K. (2006). Quantitative measurement of ocular dominance using binocular rivalry induced by retinometers. *Journal of Cataract Refractive Surgery*, 32, 831-836.
Ogle, K.N. (1962). Ocular dominance and binocular retinal rivalry. In *Chapter 18: The eye* (ed. H. Dayson), Academic Press, New York, 409-417.
Ooi, T.L. & He, Z.J. (2001) Sensory eye dominance. *Optometry*, 72, 168-177.
Valle-Inclán, F., Blanco, M.J., Soto, D. & Leirós, L. (2008) A new method to assess eye dominance. *PsicolOgica*, 29, 55-64.
(Feb. 15, 2008) Yang, Eunice, Blake, Randolph, & McDonald, Jay. A novel interocular suppression technique for measuring sensory eye dominance.

* cited by examiner

*Primary Examiner* — Huy K Mai
(74) *Attorney, Agent, or Firm* — Keisling & Pieper PLC; David B. Pieper

(57) ABSTRACT

There is disclosed apparatus and method for a test of eye dominance of human subjects for which on each 10-sec trial, one eye starts with a strong image that gets progressively weaker or does not get progressively stronger, while, at the same time, the other eye gets a weak image that gets progressively stronger. The initially strong image will always be seen at the beginning and eventually vision will flip to the other eye's view once that image has achieved sufficient strength to overcome the dominance of the initially strong stimulus (which itself is getting progressively weaker). The subject indicates recognition of the strengthening image and the time is recorded. Results show that the test provides a reliable measure of eye dominance which is seen to vary considerably among people within a sample of normal adults.

19 Claims, 4 Drawing Sheets

```
TIME        -------------------->-------------------------->----------------->
Display     T M T M T M T M T M T M T M T M T M
Viewer (1)  L R L R L R L R L R L R L R L R L R
Viewer (2)  R L R L R L R L R L R L R L R L R L
```

*FIG. 3*

```
TIME        -------------------->-------------------------->----------------->
Display     T M T M T M T M T M T M T M T M T M
Viewer (3)  L R B L R B L R B L R B L R B L R
Viewer (4)  R R L L R R L L R R L L R R L L R R L L
```

*FIG. 4*

EYE DOMINANCE EVALUATION APPARATUS AND METHOD

CROSS-REFERENCE TO RELATED APPLICATIONS

This application claims priority to and is a continuation-in-part of U.S. Provisional Patent Application No. 61/206,864 filed on Feb. 5, 2009, entitled EYE DOMINANCE APPARATUS AND METHOD (J. E. McDonald, II, Randolph Blake, Eunice Yang).

STATEMENT REGARDING FEDERALLY SPONSORED RESEARCH OR DEVELOPMENT

This work was supported by NIH grants EY13358 and 5T32 EY007135.

BACKGROUND OF THE INVENTION

I. Field of the Invention

Surgical treatment for cataract(s) represents the most common form of ocular surgery, with almost 3 million procedures performed during 2007 within the United States alone, according to the 2007 Market Scope survey. As people continue to live longer, treatment for cataracts will surely increase in incidence, at least until preventive strategies are discovered. At the same time, major advances in the design and fabrication of intraocular lenses (IOLs) provide the ophthalmologist with an expanding number of options for the patient's presbyopia.

Despite the increased reliance on multifocal and accommodating IOLs, the vast majority of lenses implanted following cataract surgery continue to be monofocal IOLs, and it is estimated that whether accommodative or non-accommodative this trend will remain true for decades to come (Linstrom, 2008). As ophthalmologists have continued to strive to relieve the cataract patient of post operative dependence on spectacle correction, the strategy of mixing and matching intraocular lenses, the timing between surgery as well as which eye to fix first centers around the selection of "ocular dominance."

New corneal solutions to refractive and presbyopic issues (Presbylasik and Acufocus) as patients preferred or dominant eye. In all of these situations ophthalmologist tends to select the dominant eye for distance and the non dominant eye for near, in part because of the belief that seeing at a distance is more important in patients' everyday lives. Putting aside the validity of this belief in the primacy of distance vision, we are more immediately concerned with the bases for deciding which eye is an individual's dominant eye in the first place.

In the clinic, an individual's dominant eye is conventionally defined using some kind of test that relies on pointing or sighting under conditions where the individual is forced to view an object with one eye (e.g., the Miles A-B-C Method: Miles, 1929). While such tests provide fairly consistent measures of dominance (as evidenced by test/retest reliability), it is arguable whether sighting dominance taps into those sensory/neural processes that are essential for maximizing coordinated binocular vision under conditions where the two eyes are receiving retinal images that differ in spatial frequency content, as they inevitably will when dealing with IOLs. It has long been known (Washburn et al, 1934) that sighting dominance tests can be affected by factors such as handedness that are extraneous for purposes of estimating sensory balance between the two eyes.

II Description of the Known Art

Several recent studies have advocated measures of interocular suppression as valid measures of eye dominance. These recent studies follow the tradition of using relative predominance during binocular rivalry as a means for indexing eye dominance, a tradition that dates back decades (see review by Porac & Coren, 1976). In one study, Valle-Inclan et al. (2008) asked individuals to view two sequences of letters rapidly presented one after the other separately to the two eyes (the authors dubbed this the dichoptic RSVP task, where RSVP stands for rapid serial visual presentation). Following each sequence, people reported whether or not a pre-specified "target" letter was seen on that trial. Some participants only saw a target letter when it was contained within the RSVP stream presented to a given eye, implying that the other eye's view was suppressed under the conditions of dichoptic stimulation; for other people, however, detection performance was equally good regardless of the eye receiving the RSVP stream containing the target, implying that both eyes' views were available to awareness for processing. This technique showed good test/retest reliability, but one has concern whether the RSVP task taps into aspects of interocular suppression plausibly engaged under more sustained viewing conditions. It is known, for example, that streams of transient stimulation can disrupt conventional binocular rivalry (Lee and Blake, 1999), which may explain why a substantial number of participants in the RSVP task described seeing two superimposed letters at the same time. The RSVP task does, however, have the advantage of using an objective performance measure—target detection—as an index of eye dominance.

In another recent study focusing on interocular suppression as an index of eye dominance, Ooi and He (2001) had participants view a briefly presented dichoptic display consisting of an array of six differently colored gratings presented separately to the two eyes; the orientation and color of gratings falling on corresponding retinal areas of the two eyes were dissimilar, creating the stimulus conditions for binocular rivalry. Rather than presenting the rival display for an extended viewing period, Ooi and He presented the array of rival gratings for just 0.33 sec, and following each presentation the participant indicated by pressing one of two keys which they saw, more "red" or more "green". Over trials the relative intensities of the gratings presented to the two eyes were adjusted to find the so-called balance point where both responses were equally likely. In their sample of several dozen people, balance point values varied from strongly right-eye dominant to strongly left-eye dominant, with some showing essentially perfect balance between the eyes. Interestingly, their measure of eye dominance was unrelated to eye dominance measured using a conventional sighting test, the Ring test (Borish, 1970).

Ooi and He's task is useful in that it permits parametric variation of stimulus strength (intensity, in their study) and stimulus characteristics such as complexity (spatial frequency in their study). However, with their task there is no objectively correct answer on any trial, meaning that each subject must figure out for himself/herself how to judge the strength of a color sensation that will vary over trials unpredictably. This kind of judgment could be confusing to explain and difficult to make for clinical patients, particularly older individuals unfamiliar with vision testing. Moreover, Ooi and He's task uses a very brief exposure duration near the lower limit for producing reliable interocular suppression (Wolfe, 1984; Leonards & Sireteanu, 1993; Blake et al, 2001). Finally, it is likely that their stimulus presentation regime effectively measures biases in initial dominance during rivalry, but it may not tap into neural events responsible for sensory eye dominance operating under more sustained viewing conditions under which the consequences of bilateral IOLs emerge.

In a similar fashion, Handa and colleagues (2004a) quantitatively assessed ocular dominance by manipulating the contrast values of the rival images until they were equally predominant. They were further able to apply this technique to monovision wearers (2004b) and to cataract patients pre- and post-operatively, with the aid of retinometers (2006). Monovision success coincided with smaller differences in contrast thresholds between the monocular images and ocular dominance measures were consistent pre- and post-surgery. In terms of disadvantages in technique, a similar argument can be made here, as with Ooi and He's paradigm. In addition, the size of the stimulus displays were large enough to induce relatively moderate amounts of 'piecemeal' rivalry, which increases response uncertainty during binocular rivalry monitoring. Measuring several contrast values for each eye also lengthens testing duration.

A variety of tests have been created to assess ocular dominance (review by Evans, 2007), and more than 25 different types of ocular dominance have also been proposed (Walls, 1951). It is no wonder, therefore, that controversy still exists over which test and type of ocular dominance are most applicable to clinical practice (Evans, 2007; Mapp, Ono & Barbeito, 2003). The types of ocular dominance and corresponding tests have been categorized into three domains: sighting dominance, sensory dominance based on persistence during binocular rivalry, and sensory dominance based on functions inherent to spatial vision, including acuity (Coren & Kaplan, 1973; Suttle et al., 2008). Assessment of dominance within and across these domains has usually lacked agreement (Suttle et al., 2008; Ooi & He, 2001; Walls, 1951; Coren & Kaplan, 1973; Seijas et al., 2007; review by Evans, 2007; Mapp, Ono, & Barbeito, 2003; Pointer, 2007). Similarly in our study, we found little consistency in dominant eye or dominance strength across the hole-in-the-card test, acuity measures, and our interocular suppression task. Overall, this suggests that, for an individual, there is no eye which is clearly superior across all visual functions, and the dominant eye may depend on the test used and function assessed (Suttle et al., 2008; Seijas et al., 2007; Mapp, Ono, & Barbeito, 2003).

One objective here is to produce a technique best suited for determining ocular dominance as a means of successfully implementing monovision with refractive surgery. Monovision correction entails the monocular "fogging" of one eye, usually the non-dominant eye, which is corrected for near vision (Evans, 2007). It is presumed that it is less demanding to suppress a blurred image in the non-dominant than the dominant eye (corrected for distance vision), thus minimizing discomfort for the subject. Indeed, there is evidence to suggest the interocular suppression occurs in monovision (Kirschen, Hung & Nakano, 1999; Simpson, 1991; Schor, Landsman & Erickson, 1987) and ocular dominance may influence one's ability to suppress anisometropic blur in monovision (Evans for review, 2007). In addition, one of the major complaints by monovision patients is the inability to suppress blurred images at night which may also account for the appearance of ghosting or haloes around lights, especially during driving (Evans, 2007). Thus, it is our intuition as well as those of many clinical practitioners that measuring interocular suppression is the most relevant approach in determining ocular dominance in that it best simulates the patients' situation after monovision correction.

Several sensory tests have been created to measure interocular suppression by presenting dissimilar stimuli dichoptically (Ogle, 1962, Collins & Goode, 1994; Ooi & He, 2001; Handa et al., 2004a,b & 2006; Valle-Inclan et al., 2008). For the reasons previously mentioned, these forms of binocular rivalry may be challenging for patients to perform and may not be reliable for a clinical setting (but see Handa et al., 2006). In contrast, our approach is more akin to the technique by Humphriss (1982) whereby individuals interocularly suppressed the lens-induced blurred image without awareness and without ever perceiving rivalry. Interestingly, within the few studies that found agreement among tests of ocular dominance, several found a correlation between sighting eye and dominant eye during rivalry or blur suppression (Spry et al., 2002; Ooi & He, 2001; Handa et al., 2004a; Schor, Landsman & Erickson, 1987; Porac & Coren, 1978). We found a similar consistency but only among individuals with significant interocular differences in suppression. Collins and Goode (1994) found that individuals with matched ocular dominance for sighting and rivalry were better at suppressing blurred information. This may imply that there is a level of suppression involved when individuals' are forced to choose one monocular view over another in a sighting test. This also highlights individual differences in the ability to suppress blur and other scene information and may be predictive of one's suppression abilities after monovision correction.

Promising evidence exists which suggests that patient's success or satisfaction with monovision correction is related to his or her ability to suppress interocular information (Evans for review, 2007). Handa and colleagues (2004b) reported that individuals with weaker sensory dominance, as determined by binocular rivalry, were more likely to be satisfied with intraocular lens monovision. Schor and colleagues (1987) reported that successful long-term monovision individuals were interocularly balanced for blur suppression. But a significant correlation between monovision success and interocular suppression has not always been found (Collins and Bruce, 1994).

Eye Dominance was one visual function to be tested in apparatus disclosed by Task, Henry L.; and Genco Louis V; Jun. 3, 1987, U.S. Statutory Invention Registration Number H293. Illustrated and described therein is a portable boxlike structure having a first and second illuminated visual displays disposed for viewing by respective left and right eyes of a subject. Among the functions to be tested is eye dominance for which the display pair includes two sets of oppositely oriented diagonal lines. There is no disclosure of separate controls for the two displays for left and right eyes.

One objective here is to produce a technique best suited for determining ocular dominance as a means of successfully implementing monovision with refractive surgery. Monovision correction entails the monocular "fogging" of one eye, usually the non-dominant eye, which is corrected for near vision (Evans, 2007). It is presumed that it is less demanding to suppress a blurred image in the non-dominant than the dominant eye (corrected for distance vision), thus minimizing discomfort for the subject. Indeed, there is evidence to suggest the interocular suppression occurs in monovision (Kirschen, Hung & Nakano, 1999; Simpson, 1991; Schor, Landsman & Erickson, 1987) and ocular dominance may influence one's ability to suppress anisometropic blur in monovision (Evans for review, 2007). In addition, one of the major complaints by monovision patients is the inability to suppress blurred images at night which may also account for the appearance of ghosting or haloes around lights, especially during driving (Evans, 2007). Thus, it is our intuition as well as those of many clinical practitioners that measuring interocular suppression is the most relevant approach in determining ocular dominance in that it best simulates the patients' situation after monovision correction.

SUMMARY OF THE INVENTION

Informed by these earlier studies and instructed by their limitations, we have devised a test and evaluation of eye dominance that isolates the sensory component of eye dominance, without any involvement in pointing or aiming or looking through small apertures with one eye. We devised a test that measured the relative "strength" of a given eye when the two eyes were placed in conflict by receiving dissimilar target and mask images whose relative strength was varied; at the same time, our test employs a forced-choice judgment that minimizes the subjective nature of the response measure. We reasoned that when someone has a strongly dominant eye, the non-dominant eye would require relatively more image contrast to overcome the influence of the contrast received by the dominant eye. Fundamentally the basis of our test is as follows: on each 10-sec trial, one eye starts with a strong image that gets progressively weaker while, at the same time, the other eye gets an image that gets progressively stronger. The initially strong image will always be seen at the beginning and eventually vision will flip to the other eye's view once that image has achieved sufficient strength to overcome the dominance of the initially strong stimulus (which itself is getting progressively weaker). The time at which a subject recognized the strengthening image is recorded.

It is an object of the invention that the apparatus to conduct the test is assembled from available components, typically a PC, a monitor, liquid crystal shutter glasses, a response pad or normal computer keyboard, and software platforms for programming the procedure, recording results and analyzing their significance.

It is another object of the invention that this measure of eye dominance gives reliable results which are shown to vary significantly among people within a sample of normal adults.

BRIEF DESCRIPTION OF THE DRAWINGS

FIG. 3 is a time chart of target and mask image presentation to left and right eyes in typical procedures.

FIG. 4 is another time chart supplemental to that of FIG. 3.

DETAILED DESCRIPTION

Figure 1:
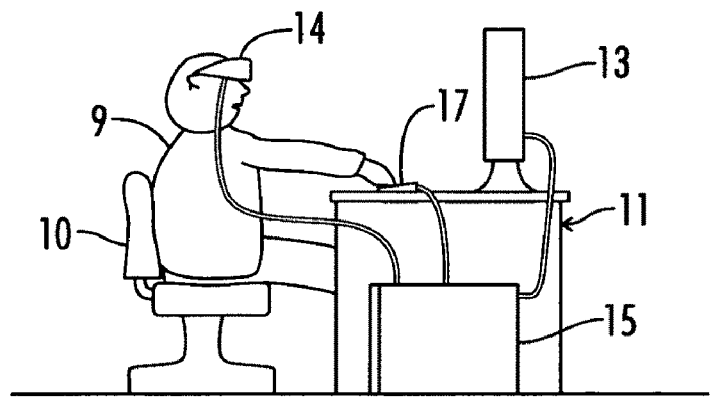
FIG. 1 is a plan view of test station apparatus and subject position according to the invention.
Figure 2:
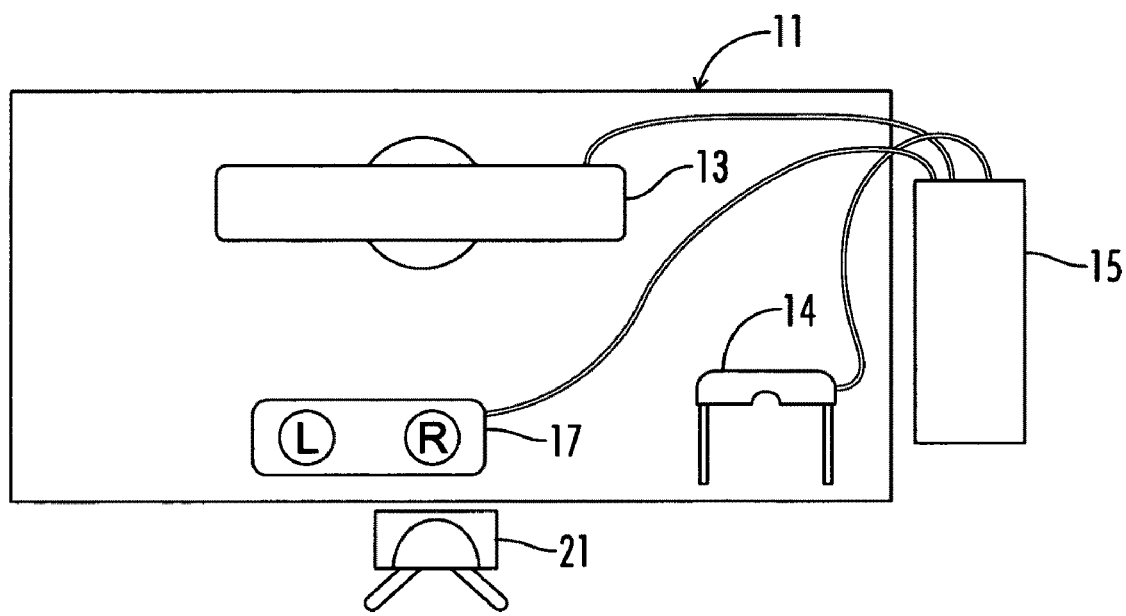
FIG. 2 is a side view of a test station similar to that of FIG. 1.

As shown in FIGS. 1 and 2, test stations 11 provided for access by a test subject 9 seated in chair 10 include a video monitor 13 connected to a personal computer 15 (PC) used as a control unit. Also connected to PC 15 is a response pad 17, serving as a subject response acceptor. Receiving a control signal from PC 15 is a viewer 14 in the form of shutter glasses to be worn by subject 9. Interconnections between computer, glasses, and response pad may be wireless, or wired as shown.

Response pad 17 may have additional controls or may be replaced or augmented by a conventional computer keyboard. The FIG. 2 embodiment is provided with an optional chin support 21.

In a preferred embodiment of the invention stimuli are presented in the center of a display on video monitor 13 (800×600 resolution; 100 Hz) against a uniform background at mean luminance and viewed at a distance of about 80-90 cm (optionally with a chin rest.) The masking display includes gray scale Mondrian patterns used as a mask image that subtended 4.3°×4.3° and are preferably normalized to 60 percent contrast (root mean square). The target stimulus normally is an image of an arrow pointing either left or right (.preferably about 67°×1.33°; 20 percent contrast, root mean square). See FIG. 5.

In an alternative embodiment, the target stimulus is a gray scale photograph of a female face (1.67°×1.17°; 15 percent contrast, root mean square) angled toward the left or the right. The location of the target stimulus may be jittered around the center coordinates of the masking display across trials to avoid fixation on one location. Black and white circles (0.33° diameter) frame the boundaries of the masking display in this embodiment. Other embodiments may involve a mask or a blank display which does not reduce in contrast while the target is increasing in contrast.

Liquid crystal shutter glasses (for example Crystal Eyes; HTTP://reald-corporate.com) are used to present the masking display and target stimulus dioptically. The presentation of the mask and the target may alternate with refreshes of the monitor. The opening and closing of the glass lenses allow the left and right eyes to view temporally alternate frames on the screen without flicker. Thus, each eye may view one of the target or mask stimuli during a given trial. The eye viewing the dynamic Mondrian mask or the target stimulus is randomized across trials. In another alternative embodiment, this masking display is replaced with a different display, preferably at mean luminance. All such procedures may be programmed in Matlab version 7.6, 2008a (http://www.mathworks.com/) and Psychtoolbox version 3 (http://psychtoolbox.org or in other available protocols compatible with PC 15.

Other methods and apparatus could be employed to present the two dissimilar images to left and right eyes within the scope of the invention. For example orthogonally polarized images could be presented to a subject wearing appropriately polarized goggles or glasses using projection or a half-silvered mirror to merge the images.

Paradigm of Method of Eye Dominance Evaluation:

Although the parameters of the test procedure are flexible, one specific program provides that at the beginning of a trial, one eye views a full contrast Mondrian mask pattern and the other eye views the target at 0% contrast (no stimulus). During a trial, the target linearly increases in contrast at a rate of 1% every 100 ms. At the same time the Mondrian pattern of the masking display linearly decreases in contrast, preferably at the same rate as the target contrast increases. Subjects are instructed to immediately indicate the direction in which the target stimulus was pointing (left vs. right) by pressing a corresponding one of two response keys. Error feedback was not given. If subjects did not detect the target stimulus while the Mondrian mask pattern was visible, the target remained on the screen at full contrast until a response was made. Trials terminated once responses were made, and reaction time (RI) and accuracy were recorded. subjects performed 10 practice trials before moving on to an extended series of record trials (either 100 trials or 50 trials, depending on time available).

Record trials took on average six to seven minutes to complete.

Figure 5:
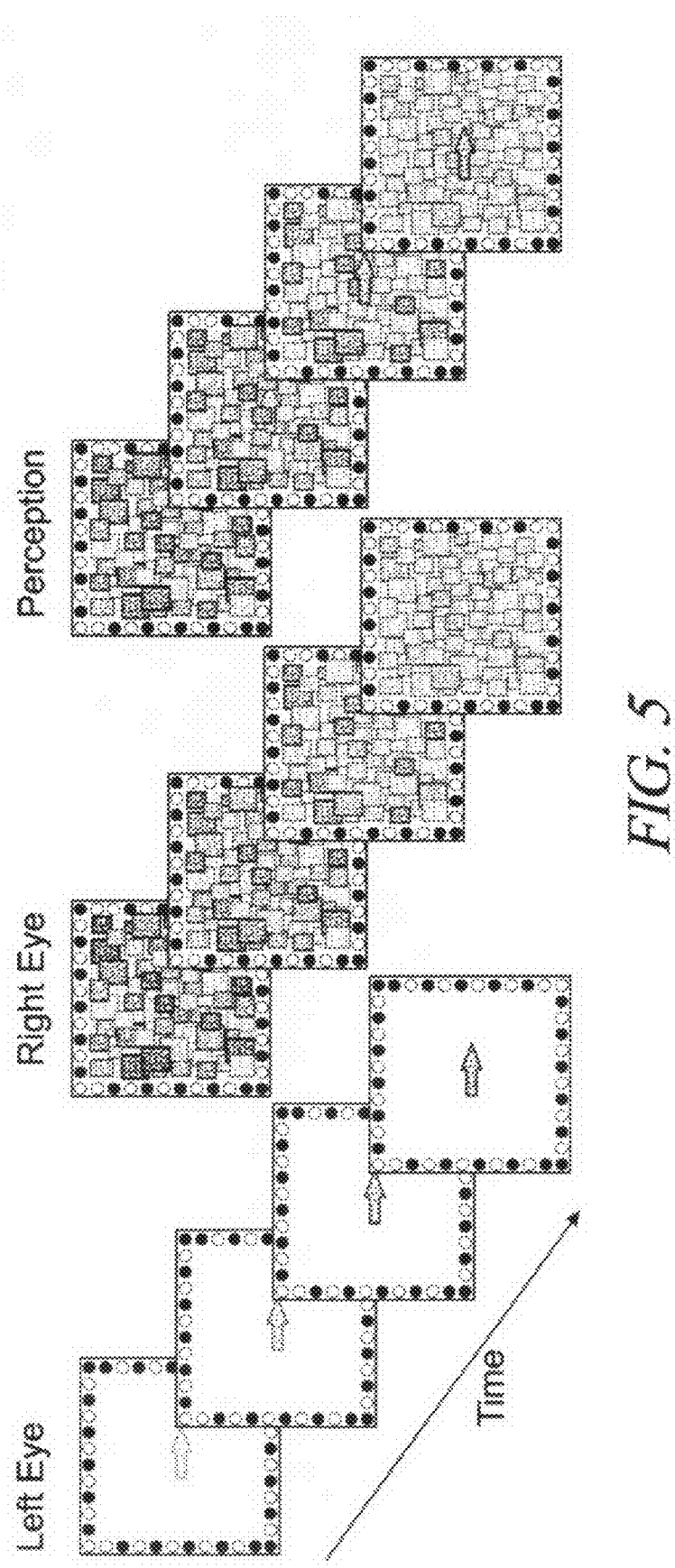
FIG. 5 is a graphic illustration of stimuli presented to eyes of the subject in a typical procedure.

Referring to FIG. 5, the left and middle columns represent the stimuli presented to each eye. During a trial, the contrast of the arrow increases and, at the same time, the contrast of the dynamic Mondrian patterns decreases. The right column represents subjects' perception during the trial. Subjects initially perceived the Mondrian display and eventually the target stimulus (in this case, the arrow) breaks suppression. Subjects respond as soon as they discriminate the direction of the target stimuli.

To quantify the results of testing a subject, an eye dominance index may be derived by calculating the ratio of mean RTs when the arrow was presented to the left eye (leRT) relative to the mean right eye RTs (reRT). The stronger sensory eye would facilitate the breakage of suppression by the target stimulus and lead to shorter reaction times in the discrimination task. On the other hand, when the sensory dominant eye is presented with dynamic noise, it more strongly suppresses the target stimulus viewed by the other eye, which produces longer RTs for identification of the direction in which the test stimulus was pointing. Hence, this particular dominance index value greater than one indicates right eye sensory dominance and dominance index value less than one indicates left eye sensory dominance. Alternative dominance indices could include a beRT for when target and mask were presented to both eyes equally. Such index value could be a numeral plus an indicator of R or L for the dominant eye.

FIG. 3 illustrates (top line) the time sequence for monitor target or mask display with the second and third lines indicating the two alternative viewer shutter openings of target or mask to left or right eye. The alternative controls produce leRT and reRT. In FIG. 4 the top line is the same as FIG. 3, but lines 2 an 3 show two different sequences usable to obtain beRT, i.e. response time in the same apparatus for subject viewing with both eyes for comparison with leRT or reRT.

In addition to the variations and modifications to the apparatus and method described herein, numerous other variations will be apparent to those skilled in the art, and the scope of the invention extends to all such variations and modifications.

CONCLUSION

We have devised and implemented a novel technique for quantifying the magnitude of interocular suppression as a means of measuring a given individual's sensory dominant eye. It offers advantages over other ocular dominance tasks for several reasons. First, the task is objectively straightforward and easy for participants to understand and perform, as evidenced by near perfect accuracy evidenced in a sample subject set. With other suppression techniques, particularly those that employ binocular rivalry, states of perceptual uncertainty associated with transition states and mixed dominance create response uncertainty; this uncertainty can be particularly problematic in that mixed dominance varies with stimulus features such as size and spatial frequency. With masking, mixed dominance rarely occurs, and the subject is not being asked to track rivalry but, instead, simply to indicate when the target emerging into dominance is sufficiently visible to report the direction in which it is pointing. Second, our task can be completed in less than 10 min, unlike other tasks that require extended test trials to assess interocular suppression. Third, the dominance measures derived here are reliable across time and with different stimulus targets. Finally, this technique provides a variable distribution of scores and is sensitive enough to measure significant interocular differences within individuals. Other studies have either failed to assess individual differences or have failed to find interocular differences.

The present apparatus and method can reliably measure interocular suppression in cataract patients pre- and post-operatively, in order to better determine the relationship between suppression and monovision success as well satisfying other needs for reliable, reproducible measurement of interocular suppression.

APPENDIX I

Experimental Results

Participants 88 observers (44 females) were recruited from the Vanderbilt University Psychology Department or through the Vanderbilt University subject pool. 23 and 21 observers also participated in Experiment 2 and 3, respectively, in addition to Experiment 1. Another 23 observers returned 1 day to 13 months later (median=8 months) to repeat the Experiment 1 in order to acquire test-retest reliability. Participants ranged in age from 18-61, with a mean age of 27 (SD=8). Approximately 10% were left handed. All participants provided written informed consent and, with the exception of 2 participants (authors), were naïve to the purpose of the study.

Acuity Measure

Far and near acuity values were measured using standardized tests provided by the Bausch and Lomb Orthorator (Rochester, N.Y.). Both eyes were presented with a diamond square, which was delineated into quadrants representing the top, bottom, left and right of the diamond. A checkerboard pattern was presented to one or both eyes and observers were instructed to indicate the quadrant in which the pattern was located (4-alternative-forced-choice); for monocular testing, the untested eye viewed only the outline of the transparent quadrants. The size of the stimulus display was smaller for each subsequent trial, for a total of 9 stimulus displays. Scores were based on the number of consecutive trials correctly answered; they were collected dioptically and dichoptically, with and without participants' corrective lenses, and for far and near acuity, for a total 12 scores per observer.

Sighting Dominance Measure

The preferred sighting eye was determined using the hole-in-the card test. A red cross (3 cm×3 cm) was presented approximately 5m in front of the observer. The observer held a card (13 cm×20 cm) with both hands, at arms length and moved the card until the cross was seen through hole in the center of the card (1.5 cm in diameter), with both eyes open. Then the observer was instructed to close one eye and report whether the cross remained in his/her line of view. The eye that allowed the observer to maintain the view of the cross while the other eye was closed was documented as the preferred sighting eye.

Sensory Eye Dominance Measure

Stimuli were presented in the center of a video monitor (800×600 resolution; 100 Hz) against a uniform background at mean luminance and viewed at a distance of 86 cm with a chin rest (FIG. 5). The CFS display (10 Hz) consisted of grayscale Mondrian patterns that subtended 4.3°×4.3° and were normalized to 60 percent contrast (root mean square). In Experiments 1 and 3, the target stimulus was an image of an arrow pointing either left or right (0.67°×1.33°; 20 percent contrast, root mean square). In Experiment 2, the target stimulus was a grayscale photograph of a female face (1.67°× 1.17°; 15 percent contrast, root mean square) angled toward the left or the right. The location of the target stimulus was jittered around the center coordinates of the CFS display across trials to avoid fixation on one location. Black and white circles (0.33° diameter) framed the boundaries of the CFS display at all times.

Liquid crystal shutter glasses (CrystalEyes; http://realdcorporate.com) were used to present the CFS display and target stimulus dioptically. The presentation of the CFS and the target stimuli alternated with every refresh of the monitor. The asynchrony between the opening and closing of the glass lenses allowed the left and right eyes to view temporally alternate frames on the screen without any sensation of flicker. Thus, each eye exclusively viewed one of the two stimuli during a given trial. The eyes viewing the dynamic Mondrian and target stimulus were counterbalanced and randomized across trials. In the case of Experiment 3, the CFS display was replaced with a blank display at mean luminance. The experiment was programmed in Matlab version 7.6, 2008a (http://www.mathworks.com/) and Psychtoolbox version 3 (http://psychtoolbox.org).

Paradigm of Experiment 1 & 2:

At the beginning of a trial, one eye viewed a full contrast Mondrian pattern and the other eye viewed the target stimulus at 0% contrast (no stimulus). During a trial, the target linearly increased in contrast at a rate of 1% every 100 ms. At the same time the Mondrian pattern comprising the CFS display linearly decreased in contrast at the same rate as the target contrast. Observers were instructed to immediately indicate the direction in which the target stimulus was pointing (left vs right) by pressing one of two response keys. Error feedback was not given. If observers did not detect the target stimulus while the Mondrian pattern was visible, the target remained on the screen at full contrast until a response was made. Trials terminated once responses were made, and reaction time (RI) and accuracy were recorded. Observers performed 10 practice trials before moving on to an extended series of experimental trials (either 100 trials or 50 trials, depending on experiment). Experiments 1 and 2 took on average, 6-7 minutes to complete.

Paradigm of Experiment 3:

The design and task of Experiment 3 were identical to that of Experiment 1 with the exception that the CFS display was replaced with a blank screen fixed at mean luminance throughout the trial. The experiment took 2 minutes on average to complete. FIG. 5: Experiment 1 paradigm. The left and middle columns represent the stimuli presented to each eye. During a trial, the contrast of the arrow increased and, at the same time, the contrast of the dynamic Mondrian patterns decreased. The right column represents observers' perception during the trial. Observers initially perceived the Mondrian display and eventually the target stimulus (in this case, the arrow) broke suppression. Observers responded as soon as they could discriminate the direction of the target stimulus.

Figure 6:
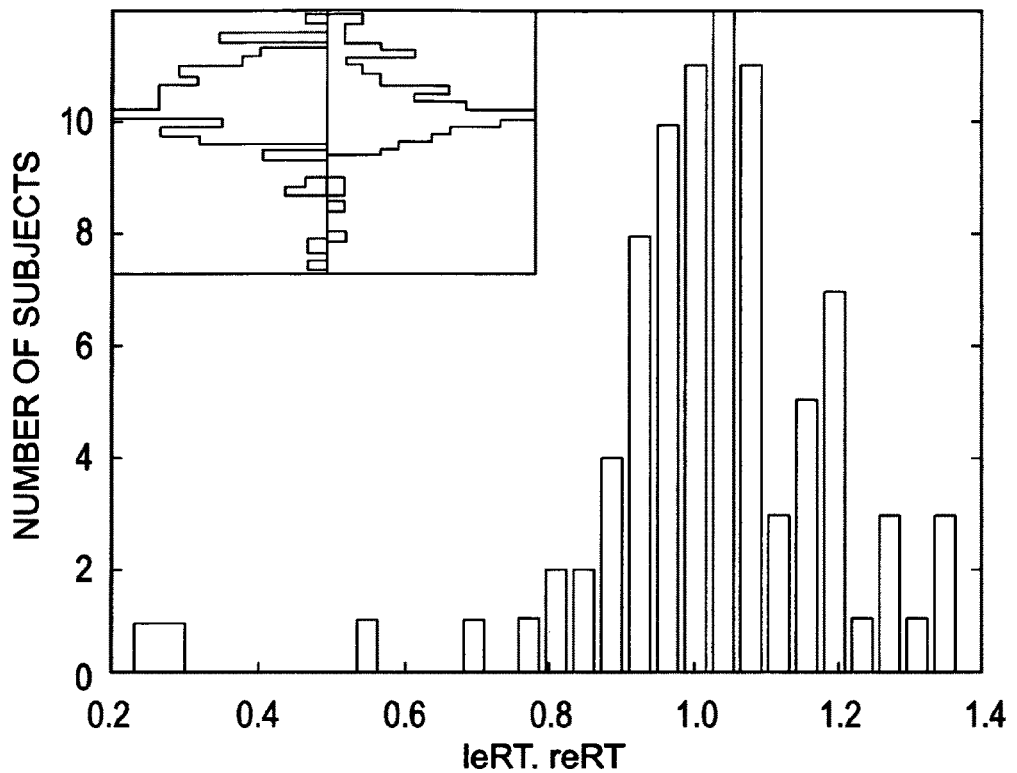
FIG. 6 is a histogram of eye dominance index for a group of subjects in one test procedure.
Figure 7:
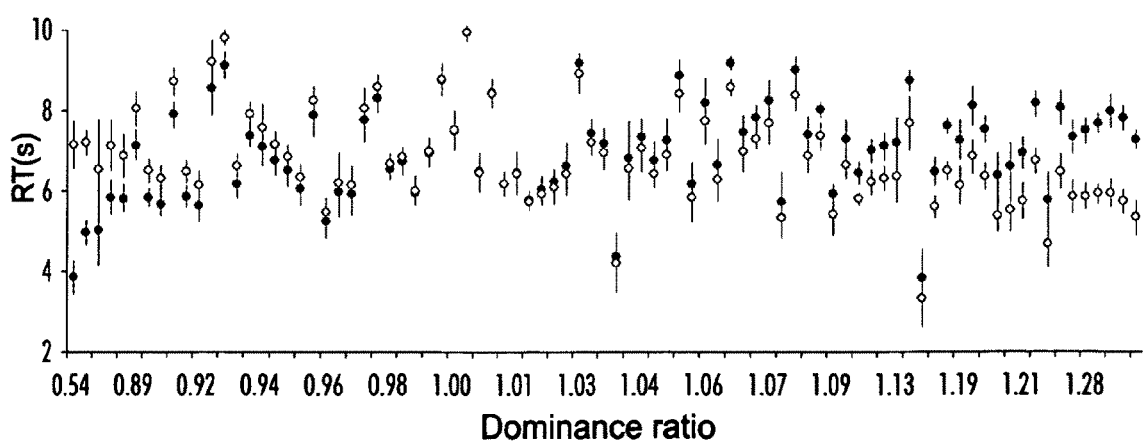
FIG. 7 is a chart of left and right eye response times for a group of subjects in a test procedure.

The principal results of the experiments are shown in FIGS. 6, 7, and 8 and are described below. Participants in Experiment 1 averaged at 98 percent correct accuracy. An eye dominance index was derived by calculating the ratio of mean RTs when the arrow was presented to the left eye (leRT) to the mean right eye RTs (reRT). The stronger sensory eye would facilitate the breakage of suppression by the target stimulus and lead to shorter reaction times in the discrimination task. In the same way, when the sensory dominant eye is presented with dynamic noise, it more strongly suppresses the target stimulus viewed by the other eye, which produces longer RTs for identification of the direction in which the test stimulus was pointing. Hence, dominance index values greater than one indicate right eye sensory dominance and dominance index values less than one indicate left eye sensory dominance.

FIG. 6 illustrates the group distribution of these eye dominance index values. The mean ratio between leRT and reRT was 1.02, and the relatively small standard deviation associated with these index values, 0.18, implies that sensory dominance was evenly distributed and relatively modest among our participants. Still, a few individuals produced results indicative of extreme eye dominance, particularly for the left eye (see inset to FIG. 6). Two were at least 3 standard deviations below the mean and their data were excluded in subsequent group analyses. Values greater than 1 indicate right eye dominance and values below 1 indicate left eye dominance. The insert in the upper left corner plots separate histograms for leRT (red) and reRT (blue).

The mean RT observed in Experiment 1 was 6.85 s (SD=1.29 s). Across observers, there was a small but statistically significant difference in condition (t(85)=2.21, p=0.03), such that participants were on average faster on trials where the arrow was presented to the right eye (reRT: M=6.74 s, SD=1.27 s) than when it was presented to the left (leRT: M=6.96 s, SD=I.32 s). Indeed, the number of participants categorized as sensory right eye dominant (62%) was significantly greater than the number of participants categorized as left eye dominant (38%) based on the dominance index (chi square=4.65, p=0.03). A similar proportion of individuals (59%) used their right eye as their preferred sighting eye, as measured with the hole-in-the-card test. However, differences in sighting dominance were not significant (chi square=3.05, p>0.05) and neither was the proportion of individuals with consistent sensory and sighting dominant eye significantly different from those who were inconsistent (chi square=0.429, p>0.05). Apparently our measure of sensory eye dominance does not tap into the same processes as those involved in sighting dominance.

We further examined whether individual differences in left eye and right eye suppression were associated with differences in acuity. However after correcting for multiple correlations, there was no significant relationship between any of the acuity scores and leRT, reRT or the dominance index.

Intra-individual interocular differences were also observed. 32 of 86 participants, i.e., 37% of those tested, showed significant differences between their leRT and reRT, based on sample t-tests. Significant differences were also consistently found on the basis of non-overlapping 95% confidence intervals (FIG. 3; Suttle et al., 2008). This suggests that our technique is sensitive enough to detect interocular differences within a large portion of our sample.

FIG. 7: shows mean RTs for left eye (filled circles) and right eye (empty circles) conditions for each participant. Participants' data are ordered by their dominance index. Error bars indicate 95% confidence intervals.

To determine the reliability of RT values across time, we conducted two separate control experiments. First, 12 observers performed 100 trials in which half of the time, the arrow was presented to one eye and the Mondrian patterns to the other. This is twice the number of trials originally administered. We compared the mean leRT and reRT for the first and last 25 trials of each condition. Although there was a main effect of block, which is the mean RT for the first 50 versus last 50 trials (F(1,11)=7.45; MSE=0.269; p=0.02), its interaction with condition was not significant (F(1,11)=0.096; MSE=0.068; p>0.05). Similarly, the dominance index was not Second, we examined test-retest reliability in 23 observers. There was a significant main effect of time (F(I,22)=4.73; MSE=0.832; p=0.04) but the interaction between time and mean RT for each condition was not significant (F(1,22)=0.224; MSE=0.191; p>0.05). Furthermore, leRT, reRT, and dominance index was significantly correlated between and test and retest (r=0.69, p<0.001; r=0.63, p<0.001; r=0.61; p=0.002, respectively). The large majority of observers maintained the same eye dominance on retest, as indicated (these individuals correspond to data points in the upper left and lower right quadrants of FIG. 8, right). Only six individuals reversed their eye dominance index, and 5 of those 6 had very small index values to begin (implying no significant eye dominance on this test). Among those observers with significant eye dominance, test-retest index values consistently implicated the same eye as the dominant eye.

We also examined whether our results could be obtained using other, more naturalistic stimuli. In Experiment 2, the arrow was replaced with an image of a woman's face angled towards the left or right. Participants were significantly slower at responding to the angle of the face than the direction of the arrow (F(1,22)=10.57; MSE=0.296; p=0.004). However, there was no interaction between the type of stimulus and condition (F(1,22)=1.3; MSE=.1; p>0.05), which indicates the pattern of RTs were similar across experiments. Furthermore, a significant correlation existed between the dominance index values measured under the arrow and face conditions(r=0.74, p<0.001). Hence, sensory eye dominance can be reliably measured with different stimuli using this interocular suppression technique.

One may wonder whether we would obtain the same results without interocular suppression, that is, presenting the arrow monocularly without a competing stimulus. This would be analogous to the measurement of contrast sensitivity. In Experiment 3, the arrow (increasing in contrast) was viewed by one eye while a blank display was viewed by the other. Participants performed the same task as in Experiment 1. We found no significant correlation between the dominance index obtained when participants performed the task with and without the CFS display.

APPENDIX II

References

Blake, R., Yang, Y. & Westendorf, D. (1991) Discriminating binocular fusion from false fusion. *Investigative Opthalmology & Visual Science*, 32, 2821-2825

Borish, I. M. (1970) *Clinical refraction, 3$^{rd}$ Edition.* Professional Press Books: Fairchild Publications, New York.

Collins, M. J. & Bruce, M. S. (1994). Factors influencing performance with monovision. *J. Br. Contact Lens Assoc.* 17, 83-89.

Collins, M. J., & Goode, A. (1994). Interocular blur suppression and monovision. *Acta Ophthalmologica,* 72(3), 376-380.

Coren, S., & Kaplan, C. P. (1973). Patterns of ocular dominance. American Journal of Optometry & Physiological Optics, 50, 283-292.

Evans, B. J. W. (2007). Monovision: a review. *Ophthalmic & physiological optics,* 27, 417-439.

Handa, T., Mukuno, K., Uozato, H., Niida, T., Shoji, N., & Shimizu, K. (2004a). Effects of dominant and nondominant eyes in binocular rivalry. *Optometry and vision science,* 81(5), 377-382.

Handa, I., Mukuno, K., Uozato, H., Niida, T., Shoji, N., Minei, R., Nitta, M., & Shimizu, K. (2004b). Ocular dominance and patient satisfaction after monovision induced by intraocular lens implantation. *Journal of Cataract Refractive Surgery,* 30, 769-774.

Handa, T., Uozato, H., Higa, R., Nitta, M., Kawamorita, T., Ishikawa, H., Shoji, N., & Shimizu, K. (2006). Quantitative measurement of ocular dominance using binocular rivalry induced by retinometers. *Journal of Cataract Refractive Surgery,* 32, 831-836

Harmon, D. (2008) Refractive IOLs—economic demographics. In *Mastering Refractive IOLs: The Art and Science*, D. F. Chang (Ed), Slack Incorp. Thorofare N.J., pp 5-6.

Humphriss, D. (1982). Binocular refraction. In *Optometry* (eds K. Edwards and R. Lewellyn), Butterworths, London, 130-149.

Kirschen, D. G., Hung CC., & Nakano, T. R. (1999). Comparison of suppression, stereo acuity, and interocular differences in visual acuity in monovision and acuvue bifocal contact lenses. *Optometry and vision science,* 76, 832-837.

Lee, S. H. & Blake, R. (1999) Rival ideas about binocular rivalry. *Vision Research,* 39, 1447-1454.

Lindstrom, R. L. (2008) Refractive survey and IOLs—future trends. In *Mastering Refractive IOLs: The Art and Science,* D. F. Chang (Ed), Slack Incorp. Thorofare N.J., pp. 13-14.

Miles, W. (1929) Ocular dominance demonstrated by unconscious sighting, *Journal of Experimental Psychology,* 12, 113-126.

Ogle, K. N. (1962). Ocular dominance and binocular retinal rivalry. In *Chapter* 18: *The eye* (ed. H. Dayson), Academic Press, New York, 409-417.

Ooi, T. L. & He, Z. J. (2001) Sensory eye dominance. *Optometry,* 72, 168-177.

Mapp, A. P., Ono, H., & Barbeito, R. (2003). What does the dominant eye dominate? A brief and somewhat contentious review. *Perception & Psychophysics,* 65(2), 310-317.

Pointer, J. S. (2007). The absence of later congruency between sighting dominance and the eye with better visual acuity. *Ophthalmic & physiological optics,* 27, 106-110.

Porac, C., & Coren, S. (1978). Sighting dominance and binocular rivalry. *American Journal of Optometry & Physiological Optics,* 55, 208-213.

Schor, C., Landsman L., & Erickson, P. (1987). Ocular dominance and the interocular suppression of blur in monovision. *American Journal of Optometry & Physiological Optics,* 64(10), 723-730.

Seijas, 0., Gomez de Liano, P., Gomez de Liano, R., Roberts, C. J., Piedrahita, E., & Diaz, E. (2007). Ocular dominance diagnosis and its influence in monovsion. *American Journal of Ophthalmology,* 144(2), 209-216.

Simpson, T. (1991). The suppression effect of simulated anisometropia. *Ophthalmic & physiological optics,* 11, 350-358.

Spry, P. G., Furber, J. E. & Harrad, R. A. (2002). The effect of ocular dominance on visual field testing. *Optometry and vision science,* 79, 93-97.

Suttle, C., Alexander, J., Liu, M., Ng, S., Poon, J., & Iran, 1. (2008). Sensory ocular dominance based on resolution acuity, contrast sensitivity and alignment sensitivity. *Clinical and Experimental Optometry.*

Valle-Inclán, F., Blanco, M. J., Soto, D. & Leirós, L. (2008) A new method to assess eye dominance. *PsicolOgica,* 29, 55-64.

Walls, G. L. (1951). A theory of ocular dominance. *Arch Ophthalmol.* 45, 387-412.

Washburn, M. F., Faison, C. & Scott, R. (1934) A comparison between the Miles A-B-C method and retinal rivalry as tests of ocular dominance. *American Journal of Psychology,* 46, 633-636.

Wolfe, J. (1983) Influence of spatial frequency, luminance, and duration on binocular rivalry and abnormal fusion of briefly presented dichoptic stimuli. Perception, 12, 447-456.

What is claimed is:

1. Apparatus for evaluating eye dominance in a human subject comprising:
   at least one display for presenting at least one target image and at least one masking image, each having separately controllable contrast;
   a viewer for directing one of said images selectively to only a first eye of said subject and for directing one of said images selectively to a second eye of said subject;
   an image controller for causing the contrast of the target image to increase with time while the contrast of the masking image decreases or does not increase with time;
   at least one subject response acceptor for receiving a subject response to visual detection of said target image;
   a computing and data processing control unit configured to coordinate said display, said viewer, and said image controller and record response times for image viewing sequences by a subject.

2. Apparatus as recited in claim 1 wherein said viewer comprises liquid crystal glasses coordinated to direct selected frames from said display to a selected eye of the subject.

3. Apparatus as recited in claim 2 wherein the control unit is programmed to control said display to present a sequence of alternating frames showing target images and masking images and said viewer is coordinated therewith to transmit alternate frames only to a first eye or only to a second eye.

4. Apparatus as recited in claim 2 wherein said masking image comprises Mondrian patterns.

5. Apparatus as recited in claim 2 wherein there are two response acceptors for selective response to two different target images.

6. Apparatus as recited in claim 5 wherein display of frame images follow with sufficient rapidity to avoid a perception of flicker.

7. Apparatus as recited in claim 5 wherein said display comprises a conventional computer type monitor located within about one meter of a subject position at which position said response acceptors are subject accessible.

8. Apparatus as recited in claim 1 wherein said masking image comprises Mondrian patterns.

9. Apparatus as recited in claim 1 wherein there are two response acceptors for selective response to two different target images.

10. Apparatus as recited in claim 1 wherein there are two target images with one being left facing and the other being right facing, and there are two response acceptors designated left and right respectively.

11. A method for evaluating eye dominance in a human subject comprising the steps of:
    presenting to a subject at least one target image and at least one masking image, each having separately controllable contrast;
    directing one of said images selectively to only a first eye of said subject and directing one of said images selectively to a second eye of said subject;
    causing the contrast of the target image to increase with time while the contrast of the masking image decreases or does not increase with time;
    providing at least one subject response acceptor for receiving a subject response to visual detection of said target image;
    using a computing and data processing control unit to coordinate said image presentation, image direction, and image contrast and record response times for image viewing sequences by a subject.

12. The method as recited in claim 11 wherein directing said images selectively to respective eyes of said subject is effected by liquid crystal glasses coordinated to direct selected image frames to a selected eye of the subject.

13. The method as recited in claim 12 wherein the control unit is programmed to present a sequence of alternating frames showing target images and masking images and said liquid crystal glasses are coordinated therewith to transmit alternate frames only to a first eye or only to a second eye.

14. The method as recited in claim 12 wherein said masking image comprises Mondrian patterns.

15. The method as recited in claim 12 wherein there are two response acceptors for selective response to two different target images.

16. The method as recited in claim 15 wherein images follow with sufficient rapidity to avoid a perception of flicker.

17. The method as recited in claim 15 wherein said images are presented on a conventional computer type monitor located within about one meter of a subject position, at which position said subject response acceptor is subject accessible.

18. The method as recited in claim 11 wherein said masking image comprises Mondrian patterns.

19. The method as recited in claim 11 wherein there are two response acceptors for selective response to two different target images.

* * * * *